US010531679B2

(12) United States Patent
Rudinger et al.

(10) Patent No.: US 10,531,679 B2
(45) Date of Patent: Jan. 14, 2020

(54) METHOD FOR DRYING BIOMASS

(71) Applicant: Evonik Degussa GmbH, Essen (DE)

(72) Inventors: Nicolas Rudinger, Düsseldorf (DE);
Christian Rabe, Grossostheim (DE);
Wilfried Blümke, Schöneck (DE)

(73) Assignee: Evonik Degussa, GmbH, Essen (DE)

( * ) Notice: Subject to any disclaimer, the term of this patent is extended or adjusted under 35 U.S.C. 154(b) by 0 days.

(21) Appl. No.: 14/904,665

(22) PCT Filed: Jul. 8, 2014

(86) PCT No.: PCT/EP2014/064569
§ 371 (c)(1),
(2) Date: Jan. 12, 2016

(87) PCT Pub. No.: WO2015/007568
PCT Pub. Date: Jan. 22, 2015

(65) Prior Publication Data
US 2016/0183565 A1   Jun. 30, 2016

(30) Foreign Application Priority Data
Jul. 16, 2013  (EP) .................................... 13176661

(51) Int. Cl.
| *A23K 10/12* | (2016.01) |
|---|---|
| *A23K 30/20* | (2016.01) |
| *A23K 10/18* | (2016.01) |
| *A23L 3/50* | (2006.01) |
| *A23J 3/34* | (2006.01) |
| *A23J 1/00* | (2006.01) |
| *A23J 3/20* | (2006.01) |
| *A23L 3/40* | (2006.01) |
| *A23J 1/18* | (2006.01) |
| *C12N 1/12* | (2006.01) |
| *A23K 40/10* | (2016.01) |
| *A23K 10/16* | (2016.01) |
| *A23K 20/158* | (2016.01) |
| *A23K 50/80* | (2016.01) |
| *A23K 1/00* | (2006.01) |
| *A23K 1/16* | (2006.01) |
| *A23K 1/18* | (2006.01) |
| *A23K 3/00* | (2006.01) |

(52) U.S. Cl.
CPC .............. *A23K 10/12* (2016.05); *A23J 1/008* (2013.01); *A23J 1/009* (2013.01); *A23J 1/18* (2013.01); *A23J 3/20* (2013.01); *A23J 3/347* (2013.01); *A23K 1/007* (2013.01); *A23K 1/008* (2013.01); *A23K 1/164* (2013.01); *A23K 1/188* (2013.01); *A23K 3/005* (2013.01); *A23K 10/16* (2016.05); *A23K 10/18* (2016.05); *A23K 20/158* (2016.05); *A23K 30/20* (2016.05); *A23K 40/10* (2016.05); *A23K 50/80* (2016.05); *A23L 3/40* (2013.01); *A23L 3/50* (2013.01); *C12N 1/12* (2013.01); *A23V 2250/1882* (2013.01); *A23V 2250/202* (2013.01); *A23V 2300/10* (2013.01); *A23V 2300/14* (2013.01)

(58) Field of Classification Search
CPC .. A23L 3/40; A23L 3/50; A23K 10/10; A23K 10/12; A23K 10/22; A23K 10/16; A23K 10/18; A23K 20/158; A23K 30/20; A23K 40/10; A23K 40/25; A23K 50/70; A23K 50/75; A23K 50/80; A23J 1/008; A23J 1/009; A23J 1/02; A23J 1/18; A23J 3/20; A23J 3/347; C12N 1/12; A23V 2250/1882; A23V 2250/202; A23V 2300/10; A23V 2300/14
USPC ....... 426/53–54, 643, 1, 443, 465–467, 805, 426/507, 312
See application file for complete search history.

(56) References Cited

U.S. PATENT DOCUMENTS

| 2,123,134 | A | * | 7/1938 | Cowgill | ................. | A23B 7/028 |
|---|---|---|---|---|---|---|
| | | | | | | 159/11.1 |
| 2,177,031 | A | * | 10/1939 | Tanner | ..................... | C21D 1/74 |
| | | | | | | 148/626 |
| 2,513,369 | A | * | 7/1950 | Shaw | ..................... | A23B 4/031 |
| | | | | | | 34/364 |
| 3,257,737 | A | * | 6/1966 | Margittai | ................. | A23B 7/02 |
| | | | | | | 34/211 |
| 3,257,738 | A | * | 6/1966 | Margittai | ................. | A23B 7/02 |
| | | | | | | 34/211 |
| 3,437,489 | A | * | 4/1969 | Arakawa | ................ | A23K 10/22 |
| | | | | | | 426/541 |

(Continued)

FOREIGN PATENT DOCUMENTS

| AU | 771 809 B2 | 6/2001 |
|---|---|---|
| CH | 646 729 | 12/1984 |

(Continued)

OTHER PUBLICATIONS

Baeverfjord, et al., "Low feed pellet water stability and fluctuating water salinity cause separation and accumulation of dietary oil in the stomach of rainbow trout (*Oncorhrynchus mykiss*)," *Aquaculture* 261(4):1335-1345 (Dec. 2006).

(Continued)

*Primary Examiner* — Drew E Becker
(74) *Attorney, Agent, or Firm* — Law Office of: Michael A. Sanzo, LLC

(57) ABSTRACT

It has been found according to the invention, that a biomass containing an oxidation-sensitive material of value may be dried under particularly mild conditions by a method in which the drying gas is passed over the biomass to be dried in cycle gas mode.

9 Claims, No Drawings

(56) References Cited

U.S. PATENT DOCUMENTS

| | | | |
|---|---|---|---|
| 3,773,527 A * | 11/1973 | Ruggerone | A23B 7/0056 426/106 |
| 3,920,815 A * | 11/1975 | Harvey | A23B 7/024 426/533 |
| 4,160,040 A | 7/1979 | Luca et al. | |
| 4,209,538 A * | 6/1980 | Woodruff | A23B 7/152 426/314 |
| 4,228,197 A * | 10/1980 | Means | A23L 3/3418 422/40 |
| 4,335,150 A * | 6/1982 | Hosaka | A23B 4/03 34/472 |
| 4,592,762 A * | 6/1986 | Babu | C10J 3/482 252/373 |
| 4,683,139 A * | 7/1987 | Cheng | A23B 4/00 426/124 |
| 5,113,597 A * | 5/1992 | Sylla | A23F 5/486 34/443 |
| 5,130,242 A * | 7/1992 | Barclay | A61K 31/20 426/49 |
| 5,298,271 A * | 3/1994 | Takashina | A23D 9/06 426/312 |
| 5,340,594 A | 8/1994 | Barclay | |
| 5,340,742 A | 8/1994 | Barclay | |
| 5,434,183 A | 7/1995 | Larsson-Backstrom | |
| 5,518,918 A | 5/1996 | Barclay | |
| 5,567,732 A | 10/1996 | Kyle et al. | |
| 5,574,065 A | 11/1996 | Trimbo | |
| 5,622,710 A | 4/1997 | Binder et al. | |
| 5,656,319 A | 8/1997 | Barclay | |
| 5,698,244 A | 12/1997 | Barclay | |
| 5,700,506 A * | 12/1997 | Mudahar | A23B 7/06 426/316 |
| 5,700,837 A | 12/1997 | Trimbo | |
| 5,840,358 A * | 11/1998 | Hofler | B01J 2/16 426/467 |
| 6,068,874 A * | 5/2000 | Grocholski | A23B 4/031 34/196 |
| 6,117,905 A | 9/2000 | Higashiyama et al. | |
| 6,158,147 A * | 12/2000 | Smith | F26B 21/001 34/168 |
| 6,166,230 A | 12/2000 | Bijl et al. | |
| 6,248,909 B1 | 6/2001 | Akimoto et al. | |
| 6,255,505 B1 | 7/2001 | Bijl et al. | |
| 6,326,037 B1 | 12/2001 | Mann et al. | |
| 6,372,460 B1 | 4/2002 | Gladue et al. | |
| 6,410,281 B1 | 6/2002 | Barclay | |
| 6,441,208 B2 * | 8/2002 | Bijl | A23D 9/00 435/132 |
| 6,451,567 B1 | 9/2002 | Barclay | |
| 6,602,690 B2 | 8/2003 | Kawashima et al. | |
| 6,607,900 B2 | 8/2003 | Bailey et al. | |
| 6,727,373 B2 | 4/2004 | Bijl et al. | |
| 6,812,009 B2 | 11/2004 | Gladue et al. | |
| 6,977,167 B2 | 12/2005 | Barclay | |
| 7,067,145 B2 | 6/2006 | Place et al. | |
| 7,259,006 B2 | 8/2007 | Komazawa et al. | |
| 7,381,558 B2 | 6/2008 | Barclay | |
| 7,514,096 B2 | 4/2009 | Haraldsson et al. | |
| 7,514,244 B2 | 4/2009 | Tanaka et al. | |
| 7,579,174 B2 | 8/2009 | Bailey et al. | |
| 7,709,236 B2 | 5/2010 | Akimoto et al. | |
| 7,723,386 B2 | 5/2010 | Akimoto et al. | |
| 7,732,170 B2 | 6/2010 | Bailey et al. | |
| 7,847,113 B2 | 12/2010 | Kawashima et al. | |
| 7,863,026 B2 | 1/2011 | Komazawa et al. | |
| 7,935,365 B2 | 5/2011 | Dror et al. | |
| 8,030,348 B2 | 10/2011 | Sampalis | |
| 8,052,992 B2 | 11/2011 | Dror et al. | |
| 8,124,384 B2 | 2/2012 | Bailey et al. | |
| 8,124,385 B2 | 2/2012 | Bailey et al. | |
| 8,129,172 B2 | 3/2012 | Barclay | |
| 8,143,310 B2 | 3/2012 | Wang | |
| 8,163,515 B2 | 4/2012 | Burja et al. | |
| 8,187,846 B2 | 5/2012 | Bailey et al. | |
| 8,207,363 B2 | 6/2012 | Apt et al. | |
| 8,216,812 B2 | 7/2012 | Bailey et al. | |
| 8,217,151 B2 | 7/2012 | Schaap et al. | |
| 8,236,854 B2 | 8/2012 | Akimoto et al. | |
| 8,241,868 B2 | 8/2012 | Higashiyama et al. | |
| 8,278,351 B2 | 10/2012 | Sampalis | |
| 8,288,133 B2 | 10/2012 | Bailey et al. | |
| 8,288,134 B2 | 10/2012 | Bailey et al. | |
| 8,334,363 B2 | 12/2012 | Hurd et al. | |
| 8,343,753 B2 | 1/2013 | Chilton et al. | |
| 8,420,349 B2 | 4/2013 | Kralovec et al. | |
| 8,900,831 B2 | 12/2014 | Rusing et al. | |
| 8,945,886 B2 | 2/2015 | Katano et al. | |
| 9,072,311 B2 | 7/2015 | Harel et al. | |
| 9,101,151 B2 | 8/2015 | Kobzeff et al. | |
| 9,414,612 B2 | 8/2016 | Apt et al. | |
| 9,493,798 B2 | 11/2016 | Higashiyama et al. | |
| 9,649,609 B2 * | 5/2017 | Alt | A23K 40/10 |
| 9,848,623 B2 | 12/2017 | Bailey et al. | |
| 2002/0110582 A1 | 8/2002 | Place et al. | |
| 2003/0143659 A1 * | 7/2003 | Bijl | A23D 9/00 435/67 |
| 2005/0129739 A1 | 6/2005 | Kohn et al. | |
| 2005/0287263 A1 * | 12/2005 | Mayer | A23J 1/14 426/482 |
| 2006/0051484 A1 | 3/2006 | Yamaguchi et al. | |
| 2006/0094089 A1 | 5/2006 | Barclay | |
| 2006/0160203 A1 | 7/2006 | Barclay | |
| 2006/0188969 A1 | 8/2006 | Barclay | |
| 2006/0265766 A1 | 11/2006 | Kyle et al. | |
| 2006/0286205 A1 | 12/2006 | Fichtali et al. | |
| 2007/0032383 A1 | 2/2007 | Newell | |
| 2007/0082008 A1 | 4/2007 | Harel et al. | |
| 2007/0092955 A1 | 4/2007 | De Laat et al. | |
| 2007/0243307 A1 | 10/2007 | Abril et al. | |
| 2007/0244192 A1 | 10/2007 | Metz | |
| 2007/0248738 A1 | 10/2007 | Abril et al. | |
| 2007/0248739 A1 | 10/2007 | Abril et al. | |
| 2008/0026128 A1 | 1/2008 | Yamaguchi et al. | |
| 2008/0032381 A1 | 2/2008 | Bailey et al. | |
| 2008/0038800 A1 | 2/2008 | Ruecker et al. | |
| 2008/0096964 A1 | 4/2008 | Subramanian et al. | |
| 2008/0166780 A1 | 7/2008 | Barclay | |
| 2008/0199923 A1 | 8/2008 | Barclay | |
| 2008/0254177 A1 * | 10/2008 | Lin | A23K 40/20 426/302 |
| 2009/0053342 A1 | 2/2009 | Streekstra et al. | |
| 2009/0064567 A1 | 3/2009 | Lippmeier et al. | |
| 2009/0136637 A1 * | 5/2009 | Janssen | A23B 4/03 426/312 |
| 2009/0182050 A1 | 7/2009 | Barrow et al. | |
| 2009/0202672 A1 | 8/2009 | Hartnell | |
| 2009/0263889 A1 | 10/2009 | Wumpelmann | |
| 2009/0274819 A1 | 11/2009 | Yamaguchi et al. | |
| 2009/0285969 A1 | 11/2009 | Schaap et al. | |
| 2010/0010088 A1 | 1/2010 | Chilton et al. | |
| 2010/0086638 A1 | 4/2010 | Kyle et al. | |
| 2010/0151112 A1 | 6/2010 | Franklin et al. | |
| 2010/0159583 A1 * | 6/2010 | Onose | C05F 17/02 435/303.3 |
| 2010/0239712 A1 | 9/2010 | Brooks et al. | |
| 2010/0266681 A1 | 10/2010 | Holmeide | |
| 2010/0285105 A1 * | 11/2010 | Radianingtyas | C12P 7/6463 424/450 |
| 2010/0297292 A1 | 11/2010 | Brooks et al. | |
| 2010/0297295 A1 | 11/2010 | Brooks et al. | |
| 2010/0297323 A1 | 11/2010 | Brooks et al. | |
| 2010/0297331 A1 | 11/2010 | Brooks et al. | |
| 2010/0303961 A1 | 12/2010 | Brooks et al. | |
| 2010/0303989 A1 | 12/2010 | Brooks et al. | |
| 2010/0303990 A1 | 12/2010 | Brooks et al. | |
| 2011/0054029 A1 | 3/2011 | Kuhrts | |
| 2011/0086128 A1 | 4/2011 | Abril et al. | |
| 2011/0117068 A1 | 5/2011 | Lang et al. | |
| 2011/0129884 A1 | 6/2011 | Luy | |
| 2011/0166228 A1 | 7/2011 | Holmeide et al. | |
| 2011/0177031 A1 | 7/2011 | Apt et al. | |
| 2011/0203168 A1 | 8/2011 | Franklin et al. | |
| 2011/0258915 A1 | 10/2011 | Subhadra | |

(56) References Cited

U.S. PATENT DOCUMENTS

| | | | |
|---|---|---|---|
| 2011/0287158 A1 | 11/2011 | Yamaguchi et al. | |
| 2012/0237578 A1 | 9/2012 | Lei et al. | |
| 2013/0045226 A1 | 2/2013 | Avgousti et al. | |
| 2013/0302470 A1 | 11/2013 | Becker et al. | |
| 2016/0227816 A1* | 8/2016 | Alt | F26B 21/08 |
| 2016/0249642 A1 | 9/2016 | Rabe et al. | |
| 2016/0255862 A1* | 9/2016 | Oelmann | A23K 40/10 |
| 2017/0121742 A1 | 5/2017 | Aijawi et al. | |
| 2017/0290356 A1 | 10/2017 | Silva et al. | |
| 2017/0295823 A1 | 10/2017 | Rabe et al. | |
| 2017/0295824 A1 | 10/2017 | Priefert et al. | |
| 2017/0298318 A1 | 10/2017 | Rabe et al. | |
| 2017/0303561 A1 | 10/2017 | Durhuus et al. | |
| 2017/0306365 A1 | 10/2017 | Rabe et al. | |

FOREIGN PATENT DOCUMENTS

| | | |
|---|---|---|
| CN | 101 999 552 | 4/2011 |
| CN | 102 687 810 | 9/2012 |
| CN | 103 070 293 | 5/2013 |
| CN | 103 385 390 | 11/2013 |
| DE | 10 2006 026 328 | 1/2008 |
| GB | 1 397 410 | 6/1975 |
| GB | 1 560 478 | 10/1976 |
| GB | 2 324 701 | 11/1998 |
| GB | 2 437 909 | 11/2007 |
| WO | WO 91/07498 | 5/1991 |
| WO | WO 94/08467 | 4/1994 |
| WO | WO 97/36996 | 10/1997 |
| WO | WO 97/37032 | 10/1997 |
| WO | WO 98/49904 | 11/1998 |
| WO | WO 01/54510 | 8/2001 |
| WO | WO 02/00035 | 1/2002 |
| WO | WO 2006/085672 | 8/2006 |
| WO | WO 2006/124598 | 11/2006 |
| WO | WO 2006/136539 | 12/2006 |
| WO | WO 2007/074479 | 7/2007 |
| WO | WO 2008/019887 | 2/2008 |
| WO | WO 2008/049512 | 5/2008 |
| WO | WO 2010/090979 | 8/2010 |
| WO | WO 2010/128312 | 11/2010 |
| WO | WO 2011/006261 | 1/2011 |
| WO | WO 2013/022485 | 2/2013 |
| WO | WO 2014/045191 | 3/2014 |
| WO | WO 2014/122087 | 8/2014 |
| WO | WO 2014/122092 | 8/2014 |

OTHER PUBLICATIONS

Carter, et al., "Potential of Thraustochytrids to Partially Replace Fish Oil in Atlantic Salmon Feeds," *Marine Biotechnology* 5:480-492 (Oct. 2002).

Hondo, et al., "*Schizochytrium limacinum* sp. nov., a new thraustochytrid from a mangrove area in the west Pacific Ocean," *Mycological Research* 102(4):439-448 (Apr. 1998).

Jain, et al., "Extracellular Polysaccharide Production by Thraustochytrid Protists," *Marine Biotechnology* 7:184-192 (published online May 2005).

Miller, et al., Replacement of fish oil with thraustochytrid *Schizochytrium* sp. L oil in Atlantic salmon parr (*Salmo salar* L) diets, *Comparative Biochemistry and Physiology, Part A* 148:382-392 (available online May 2007).

Nakahara, et al., "Production of Docosahexaenoic and Docosapentaenioc Acids by *Schizochytrium* sp. Isolated from Yap Islands," *Journal of American Oil Chemists' Society* 73(11):1421-1425 (Nov. 1996).

Prabu, et al., "Effect of sodium sulphate salinity for production of docosahexaenoic acid (DHA) by *Thraustochytrids aureum* RAK-21," *Asian Biomedicine* 6(5):693-701 (Oct. 2012).

Taxonomy Browser: *Aurantiochytrium limacinum*; taxonomy ID: 87102 (Jan. 2015).

U.S. Appl. No. 15/516,022, filed Mar. 31, 2017, Rabe.
U.S. Appl. No. 15/516,023, filed Mar. 31, 2017, Silva.
U.S. Appl. No. 15/516,024, filed Mar. 31, 2017, Priefert.
U.S. Appl. No. 15/516,038, filed Mar. 31, 2017, Rabe.
U.S. Appl. No. 15/516,044, filed Mar. 31, 2017, Rabe.
U.S. Appl. No. 15/516,058, filed Mar. 31, 2017, Durhuus.

Chen, et al., "Whole cell algae powder used for increasing docosahexanoic acid content in milk of high-yielding mammal, comprises docohexanoic acid containing algae cell slurry, emulsifier, antioxidant, filler, packaging material, dispersant and water," WPI/THOMPSON, Bd. 2011, Nr. 44, (Apr. 6, 2011); XP-002721747.

Uemura, "Synthesis and production of unsaturated and polyunsaturated fatty acids in yeast: current state and perspectives," *Appl. Microbiol. Biotechnol.* 95:1-12 (May 2012).

Visentainer, et al., "Influence of diets enriched with flaxseed oil on the α-linolenic, eicosapentaenoic and docosahexaenoic fatty acid in Nile tilapia (*Oreochromis niloticus*)," *Food Chemistry* 90:557-560 (May 2005).

International Search Report for PCT/EP2014/064569 filed Jul. 8, 2014.

English language translation of the Written Opinion of the International Searching Authority for PCT/EP2014/064569 filed Jul. 8, 2014.

English language translation of the International Preliminary Report on Patentability for PCT/EP2014/064569 filed Jul. 8, 2014.

European Search Report with partial machine translation for EP 13 17 6661 filed Jul. 16, 2013.

Asha, et al., "Effect of sea weed, sea grass and powdered algae in rearing the hatchery produced juveniles of *Holothuria* (metriatyla) *scabra*, jeager," *Proceedings of the National Symposium on Recent Trends in Fisheries*, (2004).

XP-002721747; Database WPI Thomson Scientific, London GB; (Sep. 2013).

XP-002534705; Degussa: "Product Information SIPERNAT D17," Internet citation (Sep. 2004).

U.S. Appl. No. 15/027,429, filed Apr. 5, 2016, Rabe.

Hammond, et al., "Safety Assessment of DHA-Rich Microalgae from *Schizochytrium* sp.," *Regulatory Toxicology and Pharmacology* 33(2):192-204 (Apr. 2001).

Suomalainen, et al., "The Fatty Acid Composition of Baker's and Brewer's Yeast," *Chem. Phys. Lipids* 2:296-315 (1968).

Technical Information 1251 (2017) http://www.sipernat.com/sites/lists/RE/DocumentsSI/TI-1251-AEROSIL-and-SIPERNAT-Silica-Versatile-Raw-Materials-for-Personal-Care-Formulations-EN.pdf download Apr. 11, 2018 (Year: 2017).

\* cited by examiner

METHOD FOR DRYING BIOMASS

CROSS REFERENCE TO RELATED APPLICATIONS

The present application is US national stage of international application PCT/EP2014/064569, which had an international filing date of Jul. 8, 2014, and which was published in German under PCT Article 21(2) on Jan. 22, 2015. Priority is claimed to European application EP 13176661.0, filed on Jul. 16, 2013.

The present invention relates to a method for drying of a biomass under mild conditions, particularly a biomass containing an oxidation-sensitive material of value, and also the biomass obtained by this method.

The importance of microbial cells for producing materials of value is well known to those skilled in the art. An example of such materials of value are foodstuff components, in particular lipids, such as, for example, polyunsaturated fatty acids. A particular role is played in the production of such materials of value not only by bacteria and yeasts, but in particular also by other fungi and by algae.

Certain materials of value, in particular polyunsaturated fatty acids (PUFAs), are an important component for the nutrition of humans and animals. The source originally used for omega-3 fatty acids was mostly fish. Later, it was discovered that certain microorganisms are heterotrophic producers of omega-3 fatty acids in large amounts, it being possible to influence, in an advantageous manner, the fatty acid production by selecting specific reaction parameters. Thereafter, the omega-3 fatty acids may be obtained from the cells, or else the cells may be employed directly in feedstuffs or foodstuffs in the form of biomass.

A problem when using and processing a large number of materials of value, in particular polyunsaturated fatty acids, is the fact that they are unstable to oxidative degradation: once the material of value is isolated from the cells, the risk of oxidative degradation is greatly increased since the protection afforded by the surrounding cell membrane is lost.

However, in accordance with the invention it has been found that a distinct improvement in the properties of the material of value present can be achieved even by drying the biomass comprising the material of value under mild conditions and a drying method in which gas is passed over the biomass in cycle gas mode has emerged as particularly advantageous.

The object of the present invention, therefore, may be considered as providing a mild method for drying biomass containing an oxidation-sensitive material of value.

The object according to the invention is achieved by a method for drying a biomass containing an oxidation-sensitive material of value, characterized in that the method comprises a drying step in which gas is passed over the biomass in cycle gas mode.

"Cycle gas mode" means that the gas used for the drying is passed over the biomass in a circulating manner.

In the method step which consists in passing gas over the biomass in cycle gas mode, said method is preferably a thermal method. This means that the gas used preferably has a temperature above the saturation temperature of the solvent to be evaporated.

The gas used is preferably air having a reduced oxygen content.

The gas conducted in cycle gas mode preferably has an oxygen content of less than 20% by weight, preferably less than 15% by weight, particularly from 5 to 13% by weight.

The gas is preferably generated by passing air over a burner and heating it in this manner. The oxygen content of the air is thereby reduced at the same time to less than 20% by weight, preferably less than 15% by weight, particularly from 5 to 13% by weight. The gas is constantly adjusted in the same manner in order to generate a constant gas flow with reduced oxygen content.

In the drying step, in which the gas in cycle gas mode is used for drying the biomass, the drying is preferably conducted in a fluidized bed process. In this drying step, the biomass is particularly preferably converted directly into a granulate, such that said step is a spray granulation process.

A particular advantage of this method consists in that biomass present in the fermentation broth can be dried and granulated in one step and therefore only one step is required from the fermentation broth containing biomass to the finished product.

A further advantage of this method consists in that the fluidized bed process may be operated in continuous and static mode: fermentation broth containing biomass may be continuously sprayed in and the finished product may be continuously discharged. Preferably, the preparation of an on-spec product without addition of additives is also possible in this context.

In this context, in the method according to the invention, the fluidized bed preferably has a temperature of 45 to 95° C., particularly 45 to 75° C., particularly preferably 45 to 60° C., particularly 50 to 60° C. The air is correspondingly heated strongly enough that a temperature of 45 to 95° C., particularly 45 to 75° C., particularly preferably 45 to 60° C., particularly 50 to 60° C. is reached in the fluidized bed.

As an alternative to the spray granulation method mentioned above, a fluidized bed granulation as a fluidized bed process, for example, may also be carried out. However, it is generally required in this case that the fermentation broth containing biomass is initially converted into a solid product, by spray-drying for example.

Fluidized bed systems which may be used in methods according to the invention are obtainable, for example, from Glatt GmbH, Germany.

The biomass to be employed in accordance with the invention comprises cells but may also contain other components. The biomass preferably takes the form of the product of a fermentative culturing process. Accordingly, the biomass may comprise not only the cells but also components of the fermentation medium. These components may take the form of, in particular, salts, antifoam agents and unreacted carbon source and/or nitrogen source. The cell content in this biomass amounts to preferably at least 70% by weight, preferably at least 75% by weight. If appropriate, the cell content in the biomass may be increased by suitable wash steps to, for example, at least 80 or at least 90% by weight before carrying out the drying process. However, the biomass obtained from the fermentation process may also be employed directly in the drying process.

Cells present in the biomass may take the form of cells which already naturally produce materials of value, preferably lipids, in particular PUFAs, but may also take the form of cells which have been made capable of producing lipids, in particular PUFAs, by means of suitable genetic engineering methods. In this context, the production may be autotrophic, mixotrophic or heterotrophic.

The biomass preferably comprises cells which produce lipids, in particular PUFAs, heterotrophically. According to the invention, the cells are preferably algae, fungi, in particular yeasts, or protists; however, cells from oil-producing plants are, for instance, also suitable. The cells are especially preferably microbial algae or fungi.

Cells of oil-producing plants which are particularly suitable are the seeds of soybeans, flax, oil seed rape, maize, cotton, safflower and sunflower.

Suitable cells of oil-producing yeasts are, in particular, strains of *Yarrowia, Candida, Rhodotorula, Rhodosporidium, Cryptococcus, Trichosporon* and *Lipomyces*.

The biomass according to the invention preferably comprises cells from the taxon *Labyrinthulomycetes* (*Labyrinthulea*, slime nets), in particular those from the family Thraustochytriaceae. The family of the Thraustochytriaceae includes the genera *Althornia, Aplanochytrium, Elnia, Japonochytrium, Schizochytrium, Thraustochytrium* and *Ulkenia*. The biomass particularly preferably comprises cells from the genera *Thraustochytrium*, or *Schizochytrium*, above all those from the genus *Schizochytrium*.

The term "*Schizochytrium*" according to the invention also includes the new genera *Aurantiochytrium* and *Oblongichytrium* which have recently emerged through the reclassification of the genus *Schizochytrium*. A particularly preferred species of *schizochytria* used in accordance with the invention is *Schizochytrium limacinum* (now: *Aurantiochytrium limacinum*), particularly from the *Schizochytrium limacinum* SR21 strain.

The oxidation-sensitive material of value is preferably an oxidation-sensitive lipid, particularly an unsaturated fatty acid, particularly preferably a polyunsaturated fatty acid (PUFA) or highly-unsaturated fatty acid (HUFA).

The cells present in the biomass are preferably distinguished by the fact that they contain at least 20% by weight, preferably at least 30% by weight, in particular at least 40% by weight, of material of value, preferably of lipids, especially preferably of PUFAs, in each case based on cell dry matter.

In a preferred embodiment, the majority of the lipids in this case is present in the form of triglycerides, with preferably at least 50% by weight, in particular at least 75% by weight and, in an especially preferred embodiment, at least 90% by weight of the lipids present in the cell being present in the form of triglycerides.

Furthermore, the lipids present in the cell preferably comprise polyunsaturated fatty acids (PUFAs), with preferably at least 10% by weight, in particular at least 20% by weight, especially preferably 20 to 60% by weight, in particular 20 to 40% by weight, of the fatty acids present in the cell being PUFAs.

According to the invention, polyunsaturated fatty acids (PUFAs) are understood to mean fatty acids having at least two, particularly at least three, C—C double bonds. According to the invention, highly-unsaturated fatty acids (HUFAs) are preferred among the PUFAs. According to the invention, HUFAs are understood to mean fatty acids having at least four C—C double bonds.

The PUFAs may be present in the cell in free form or in bound form. Examples of the presence in bound form are phospholipids and esters of the PUFAs, in particular monoacyl-, diacyl- and triacylglycerides. In a preferred embodiment, the majority of the PUFAs is present in the form of triglycerides, where preferably at least 50% by weight, in particular at least 75% by weight and, in an especially preferred embodiment, at least 90% by weight of the PUFAs present in the cell are present in the form of triglycerides.

Preferred PUFAs are omega-3 fatty acids and omega-6 fatty acids, with omega-3 fatty acids being especially preferred. Preferred omega-3 fatty acids in this context are eicosapentaenoic acid (EPA, 20:5ω-3), in particular (5Z,8Z, 11Z,14Z,17Z)-eicosa-5,8,11,14,17-pentaenoic acid, and docosahexaenoic acid (DHA, 22:6ω-3), in particular (4Z, 7Z,10Z,13Z,16Z,19Z)-docosa-4,7,10,13,16,19-hexaenoic acid, with docosahexaenoic acid being especially preferred.

Processes for production of biomass, particularly biomass which contains cells comprising lipids, particularly PUFAs, particularly from the order Thraustochytriales, are described extensively in the prior art. As a rule, the production takes place by cells being cultured in a fermenter in the presence of a carbon source and of a nitrogen source. In this context, biomass densities of more than 100 grams per litre and production rates of more than 0.5 gram of lipid per litre per hour may be attained (WO 01/54510). The process is preferably carried out in what is known as a fed-batch process, i.e. the carbon and nitrogen sources are fed in incrementally during the fermentation. When the desired biomass has been obtained, lipid production may be induced by various measures, for example by limiting the nitrogen source, the carbon source or the oxygen content or combinations of these (WO 01/54510).

Preferably, the cells are fermented in a medium with low salinity, in particular so as to avoid corrosion. This can be achieved by employing chlorine-free sodium salts as the sodium source instead of sodium chloride, such as, for example, sodium sulphate, sodium carbonate, sodium hydrogen carbonate or soda ash. Preferably, chloride is employed in the fermentation in amounts of less than 3 g/l, in particular less than 500 mg/l, especially preferably less than 100 mg/l.

Suitable carbon sources are both alcoholic and non-alcoholic carbon sources. Examples of alcoholic carbon sources are methanol, ethanol and isopropanol. Examples of non-alcoholic carbon sources are fructose, glucose, sucrose, molasses, starch and corn syrup.

Suitable as nitrogen source are both inorganic and organic nitrogen sources. Examples of inorganic nitrogen sources are nitrates and ammonium salts, in particular ammonium sulphate and ammonium hydroxide. Examples of organic nitrogen sources are amino acids, in particular glutamate, and urea.

In addition, inorganic or organic phosphorus compounds and/or known growth-stimulating substances such as, for example, yeast extract or corn steep liquor, may also be added so as to have a positive effect on the fermentation.

The cells are preferably fermented at a pH of 5 to 11, in particular 6 to 10, and preferably at a temperature of at least 20° C., in particular 20 to 40° C., especially preferably at least 30° C. A typical fermentation process takes up to approximately 100 hours.

After the fermentation has ended, the biomass is harvested. After harvesting the biomass or even optionally shortly before harvesting the biomass, the cells are preferably pasteurised in order to kill the cells and to inactivate enzymes which might promote lipid degradation. The pasteurisation is preferably effected by heating the biomass to a temperature of 50 to 121° C. for a period of 5 to 60 minutes.

Likewise, after harvesting the biomass or even optionally shortly before harvesting the biomass, antioxidants are preferably added in order to protect the material of value present in the biomass from oxidative degradation. Preferred antioxidants in this context are BHT, BHA, TBHA, ethoxyquin, beta-carotene, vitamin E and vitamin C. The antioxidant, if used, is preferably added in an amount of 0.01 to 2% by weight.

In a first step, a portion of the fermentation medium may now already be separated from the biomass and the solid fraction can thus be increased. This may be carried out in particular by centrifugation, filtration, particularly ultrafiltration or microfiltration, decanting and/or solvent evaporation. In this case the solvent is preferably evaporated using a rotary evaporator, a thin film evaporator or a falling-film evaporator in a single stage or multistage process. A useful alternative to solvent evaporation is, for example, reverse osmosis for concentrating the fermentation broth.

In this first optional but preferred step, the fermentation medium is preferably concentrated to a solid content of at least 10 or 15% by weight, preferably of at least 20 or 25% by weight, particularly 10 to 50 or 15 to 45% by weight, particularly preferably 20 to 40% or 25 to 40% by weight.

This means that the biomass to be dried in a method according to the invention is preferably present in the form of a suspension having the solid fraction stated above, where the liquid component of the suspension is preferably a fermentation broth or concentrated fermentation broth.

After concentration or partial removal of the fermentation broth, the biomass is dried in accordance with the invention by passing preferably heated gas over the biomass or biomass suspension in cycle gas mode.

Alternatively, the biomass may also be dried by a cycle gas process directly after harvesting, particularly if the fermentation broth obtained already has a high solid content, preferably as stated above.

As already mentioned, air in which the oxygen concentration has been reduced, preferably as stated above, is preferably used for drying.

The suspension is preferably dried to a residual moisture content of at most 10% by weight, particularly 0 to 10% by weight, particularly preferably at most 8% by weight, particularly 0.5 to 8% by weight, above all at most 6 or 5% by weight, particularly 1 to 6 or 1 to 5% by weight, by drying the biomass in cycle gas mode.

As already stated above, the drying of the biomass according to the invention is preferably carried out in a fluidized bed granulation process. The fermentation broth comprising biomass is to this end sprayed into the fluidized bed granulation drying system. A granulation drying system which can preferably be used according to the invention is shown schematically in FIG. 1 of EP 0809940.

The drying gas is introduced from below into the fluidized bed granulation drying system. The majority of the moisture in the injected fermentation broth evaporates and the granulate formed is maintained suspended by the gas flow of the drying gas. In this state, the particles are separated from one another and in this manner are freely accessible to the droplets when further liquid is sprayed into the bed. Also in this state, the heat and mass transfer between the solid particles and the gas flow is intensive. Product particles of the desired size are continuously removed from the fluidized bed in a classical offtake.

The fluidized bed or the bed of particles, which must be present at the beginning of the fluidized bed granulation drying process, preferably consists of dried particles of the biomass used for drying, for example, from a batch of a previous run. It is, however, equally possible to use another material as fluidized bed for initiating the fluidized bed granulation drying process.

A particular advantage of the fluidized bed granulation process is that the process can be operated continuously and the fermentation broth comprising biomass can be converted to a product having the desired particle size in one step.

The particles produced additionally have an excellent consistency and have very good bulk properties and flow characteristics due to their essentially round shape. The particles also have a low residual moisture content.

A free-flowing, fine-grained or coarse-grained product, preferably a granulate, is preferably obtained by the drying process according to the invention. A product having the desired particle size can optionally be obtained from the granulate by sieving or dust separation.

Providing a free-flowing fine-grained powder was obtained, this can optionally be converted into a coarse-grained, free-flowing and largely dust-free product, which can be stored, by suitable compacting or granulating processes.

Conventional organic or inorganic auxiliaries or supports such as starch, gelatine, cellulose derivatives or similar substances, which are typically used in food processing or feed processing as binding agents, gelling agents or thickeners, may optionally be used for the granulation or compaction.

"Free-flowing" according to the invention is understood to mean a powder that can flow out unhindered from a series of glass efflux vessels having different size outflow openings, at least from a vessel having a 5 millimeter opening (Klein: Seifen, Öle, Fette, Wachse 94, 12 (1968)).

"Fine-grained" according to the invention is understood to mean a powder having a predominant fraction (>50%) of particle sizes of 20 to 500 micrometers in diameter.

"Coarse-grained" according to the invention is understood to mean a powder having a predominant fraction (>50%) of particle sizes of 500 to 2500 micrometers in diameter.

"Dust-free" according to the invention is understood to mean a powder that contains only a low fraction (<5%) of particle sizes below 100 micrometers.

Grain or particle size is preferably determined according to the invention by laser diffraction spectrometric methods. The methods to be used are described in the textbook "Teilchengrößenmessung in der Laborpraxis" by R. H. Müller and R. Schuhmann, Wissenschaftliche Verlagsgesellschaft Stuttgart (1996) and also in the text book "Introduction to Particle Technology" by M. Rhodes, published by Wiley & Sons (1998). Inasmuch as various methods can be used, the first-cited usable method from the text book of R. H. Müller and R. Schuhmann for the determination of particle size is preferred.

The products obtained according to the invention preferably have a fraction of at least 80% by weight, particularly at least 90% by weight, particularly preferably at least 95% by weight, above all at least 97% by weight, of particles having a particle size of 100 to 3500 micrometers, preferably 1000 to 3000 micrometers, above all 1500 to 2500 micrometers.

Owing to the preparation process, preferably at least 50% by weight, particularly at least 70% by weight, particularly preferably at least 90% by weight, above all essentially all particles are formed essentially spherical in shape. Especially the formation of essentially spherical particles accounts for the excellent bulk properties and flow characteristics of the product according to the invention.

"Formed essentially spherical in shape" is understood to mean, in accordance with the invention, that the diameter of a particle is essentially uniform in all spatial directions. "Essentially uniform" is understood to mean here that the variance of the diameter of a particle in any two spatial directions is at most 20%, preferably at most 15%, particularly at most 10%, particularly preferably at most 5%.

The fraction of dust, i.e. particles having a particle size of less than 100 micrometers, is preferably at most 1% by weight, particularly preferably at most 0.5% by weight.

The bulk density of the product according to the invention is preferably from 400 to 800 kg/m$^3$, particularly preferably from 450 to 700 kg/m$^3$.

An object of the invention, therefore, is also a particulate biomass which may be obtained by a method according to the invention and also a particulate biomass which comprises oxidation-sensitive material of value, having the properties mentioned above, in particular having the properties mentioned above with respect to particle size and particle distribution. In terms of the preferred nature of the biomass and the preferred material of value present, reference is made to that previously discussed.

The biomass obtained according to the invention may be used in various ways. After drying of the biomass in accordance with the invention, the dried biomass is preferably stored or packed. The biomass can subsequently be used, for example, to manufacture foodstuff or feedstuff or to isolate the material of value from the biomass.

A feedstuff or foodstuff comprising a particulate biomass according to the invention is a further object of the present invention.

A further object of the present invention, therefore, is also a method for isolating the material of value from a particulate composition according to the invention.

In order to increase the bioavailability in the feedstuff or foodstuff to be produced and/or to facilitate the isolation of the material of value present in the biomass, the particulate biomass is preferably subjected to a cell-disruption process. The material of value may alternatively also be isolated directly from the particulate biomass without said prior disruption.

A cell suspension is preferably prepared, based on the dried biomass, before carrying out the cell-disruption method. For this purpose, the dried biomass is mixed with water or an aqueous solution in order to prepare a cell suspension having a moisture content of preferably at least 30% by weight, particularly 30 to 90% by weight, particularly preferably 40 to 80% by weight, above all 50 to 75% by weight.

The cells may be subsequently disrupted using the cell disruption methods known to those skilled in the art, such as by using a screw extruder, a beater mill, an air-nozzle mill or by applying an elevated pressure, for example by what is known as the French Press method. Alternatively or additionally, the cells may be disrupted by using cell wall digesting enzymes.

The cell disruption is preferably carried out in accordance with the invention by using a rotor-stator system. The rotor-stator system is based on a stationary part, referred to as the stator, and a rotating part, the rotor. The rotor typically has a circumferential speed of at least 5 m/s, for example 10 to 30 m/s, and the gap between rotor and stator may be for example 0.1-0.5 mm. To disrupt the cells, the cell suspension is placed into the gap between stator and rotor. The cells are subjected to a shear stress in the gap and, additionally, turbulences are caused. These two factors bring about the disruption of the cells. In a preferred embodiment, the suspension is prepared in the rotor-stator system using a solid mixing attachment. A solid mixing attachment in this context is understood to mean a device which allows the separate introduction of solid on the one hand and water or aqueous solution on the other hand into the rotor-stator system. The suspension is therefore prepared only during the cell disruption or immediately before the cell disruption by mixing in the solid mixing attachment. In accordance with the invention, it has been found that, by using such a solid mixing attachment, suspensions with very high solid contents may be subjected to the cell disruption process, which is particularly advantageous with respect to the subsequent processing. Suspensions, used when a solid mixing attachment is used in the rotor-stator system, preferably have a solid content of 20-50% by weight, particularly preferably of 30-50% by weight.

If an aqueous solution is used to prepare the cell suspension, it may comprise in particular other foodstuff components—such as vitamins or salts.

According to the invention, the energy input into the cells, particularly when using a rotor-stator system, is preferably at most 50 kWh per tonne of suspension, particularly at most 40, 35 or 30 kWh per tonne of suspension, particularly preferably at most 25, 20 or 15 kWh per tonne of suspension. Preferred ranges in this context are energy inputs of 0.1-50 kWh per tonne of suspension, particularly 0.3-45 kWh, particularly preferably 0.5-40 kWh, particularly 0.8-35 kWh, above all 1-30 kWh, particularly 1.5-25 kWh, 2-20 kWh or 3-15 kWh, in each case per tonne of suspension.

The "cell disruption rate" of the process according to the invention is preferably at least 50%, particularly preferably at least 60, 70 or 80%, above all at least 85, 90 or 95%. The "cell disruption rate" is understood to mean the number of disrupted cells, after the end of the cell disruption process, as a ratio to the total number of cells. The cell disruption rate may be determined visually, for example, using a microscope, as the ratio of the number of disrupted cells relative to the total number of cells.

To stabilize the materials of value, particularly lipids, against oxidative degradation, the cell suspension used for the cell disruption may additionally comprise antioxidants. Preferred antioxidants in this context are BHT, BHA, TBHA, ethoxyquin, beta-carotene, vitamin E and vitamin C. The antioxidant, if used, is preferably present in an amount of 0.01 to 2% by weight. In a preferred embodiment, the antioxidants in this case are already added to the fermentation medium after completion of the fermentation.

The material of value may be isolated from the biomass either proceeding from the intact dried biomass or proceeding from the disrupted biomass.

The material of value may be isolated from the disrupted biomass, for example, by a simple mechanical removal of the cell debris, for example by decanting, filtration or centrifugation.

The material of value can otherwise be isolated both from the intact and also from the disrupted biomass, for example, by solvent extraction. Once the material of value has been separated off, accordingly, the solvent can be removed, for example by applying reduced pressure. Alternatively, the material of value can be isolated, for example, by supercritical fluid extraction.

The solvents used may be the solvents known to those skilled in the art, for example, chloroform, ether, hexane, methylene chloride or methanol. The oil may also be separated, for example, by using a different oil for extracting the oil according to the invention.

The oil may subsequently be subjected to chemical or physical refining. Refining may comprise degumming, bleaching, filtering, deodorizing and/or polishing of the crude oil. Individual oil components may then optionally be isolated.

Both the intact and the disrupted biomass and also the materials of value isolated from the biomass may be used to prepare a foodstuff or feedstuff, in which the biomass or the material of value are preferably mixed with other foodstuff or feedstuff ingredients and are subsequently processed to form the foodstuff or feedstuff.

The mixture of biomass and other foodstuff or feedstuff ingredients are processed in a preferred embodiment by an extrusion process, in order to produce portions of foodstuff or feedstuff ready for sale. Alternatively, a pelleting method may also be used.

A screw or twin-screw extruder is preferably employed in the extrusion process. The extrusion process is preferably carried out at a temperature of 80-220° C., particularly 100-190° C., a pressure of 10-40 Bar, and a shaft rotational speed of 100-1000 rpm, particularly 300-700 rpm. The residence time of the mixture introduced is preferably 5-30 seconds, in particular 10-20 seconds.

In a mode of the extrusion process which is preferred in accordance with the invention, the process comprises a compacting step and a compression step.

It is preferred to intimately mix the components with each other before carrying out the extrusion process. This is preferably carried out in a drum equipped with vanes. In this mixing step, a preferred embodiment includes the injection of steam, in particular so as to bring about the swelling of the starch which is preferably present.

Before being mixed with the disrupted cells, the further foodstuff or feedstuff ingredients are preferably comminuted—if required—so as to ensure that a homogeneous mixture is obtained in the mixing step. The comminuting of the further foodstuff or feedstuff ingredients may be carried out, for example, using a hammer mill.

A process which is preferred in accordance with the invention for preparing foodstuff or feedstuff therefore comprises the following steps:

a) preparing a biomass, preferably by fermenting fungi or microalgae, which produce a material of value, preferably a lipid, particularly preferably omega-3 fatty acids;

b) drying of the biomass obtained under mild conditions, wherein the drying under mild conditions comprises passing over gas in cycle gas mode and where the oxygen content of the gas is preferably less than 20% by weight, in particular less than 15% by weight, particularly preferably 5 to 13% by weight and the previously described spray granulation process is preferably used for the drying;

c) mixing the biomass and/or materials of value isolated therefrom, optionally after carrying out a prior cell disruption process, with other foodstuff or feedstuff ingredients;

d) preparing the final product by a compacting or extrusion process.

A very particularly preferred method in accordance with the invention for preparing a foodstuff or feedstuff comprises in this case the following steps:

a) preparing a biomass, preferably by fermenting fungi or microalgae, above all slime nets, which produce a material of value, preferably a lipid, particularly preferably omega-3 fatty acids;

b) drying under mild conditions the biomass obtained to a moisture content of preferably less than 15% by weight, preferably less than 10% by weight, in particular 1-9% by weight, particularly preferably less than 5% by weight, particularly 1-4.5% by weight, wherein the drying under mild conditions comprises passing over gas in cycle gas mode and wherein the oxygen content of the gas in this case is preferably less than 20% by weight, in particular less than 15% by weight, particularly preferably 5 to 13% by, weight and the previously described spray granulation process is preferably used for the drying;

c) converting the biomass into a cell suspension having a moisture content of at least 30% by weight, preferably 30 to 90% by weight, particularly preferably 40 to 80% by weight, in particular 50 to 75% by weight;

d) disrupting the cells, preferably employing an energy input of no more than 50 kWh per tonne of suspension, preferably 0.1-50 kWh, particularly 0.3-45 kWh, particularly preferably 0.5-40 kWh, particularly 0.8-35 kWh, above all 1-30 kWh, particularly 1.5-25 kWh, 2-20 kWh or 3-15 kWh, in each case per tonne of suspension, preferably using a rotor-stator system;

e) mixing the disrupted cells and/or materials of value isolated therefrom with other foodstuff or feedstuff ingredients;

f) preparing the final product by means of a compacting or extrusion process.

Preferred methods for preparing a foodstuff or feedstuff according to the invention are preferably characterized in that the energy input to the biomass is no higher than 50 kWh per tonne of suspension in any method step. The energy input to the biomass is preferably at most 40 or 35 kWh, particularly at most 30 or 25 kWh, particularly preferably 20 or 15 kWh, in each case per tonne of suspension. This additionally ensures that the material of value present is adversely affected as little as possible.

The disrupted cells preferably account for 0.5-20% by weight, particularly 1-10% by weight, preferably 2-8% by weight of the foodstuff or feedstuff or of the composition used for preparing the foodstuff or feedstuff.

The foodstuff or feedstuff is preferably a product for use in aquaculture or a foodstuff or feedstuff for use in poultry production, pig production or cattle production. The feedstuff may also take the form of a feedstuff which is employed for growing small organisms which may be employed as feedstuff in aquaculture. The small organisms may take the form of, for example, nematodes, crustaceans or rotifers. The feedstuff is preferably present in the form of flakes, spheres or tablets. A feedstuff obtainable by extrusion has a moisture content of preferably less than 5% by weight, especially preferably 0.2 to 4% by weight.

The other foodstuff or feedstuff ingredients are preferably selected from protein-containing, carbohydrate-containing, nucleic-acid-containing and lipid-soluble components and, if appropriate, further fat-containing components and furthermore from among other additives such as minerals, vitamins, pigments and amino acids. Besides, structurants may also be present, besides nutrients, for example so as to improve the texture or the appearance of the feedstuff. Furthermore, it is also possible to employ, for example, binders so as to influence the consistency of the feedstuff. A component which is preferably employed and which constitutes both a nutrient and a structurant is starch.

The following examples may be employed as protein-containing component which additionally contains fats: fish meal, krill meal, bivalve meal, squid meal or shrimp shells. As an alternative, fish oil may also be employed as a fat-containing component. A vegetable oil may also be employed as a fat-containing component, in particular oil from soybeans, rapeseed, sunflower kernels and flax seed. An example of a carbohydrate-containing component which may be employed is wheat meal, sunflower meal, soya meal or cereal gluten.

The total oil content in the feedstuff—including the oil from the oil-containing cells—amounts preferably to 15-50% by weight.

The feedstuff for use in aquaculture is preferably used for breeding finfish and crustaceans which are preferably intended for human nutrition. These include, in particular, carp, tilapia, catfish, tuna, salmon, trout, barramundi, bream, perch, cod, shrimp, lobster, crabs, prawns and crayfish. It is especially preferably a feedstuff for salmon farming. Preferred types of salmon in this context are the Atlantic salmon, red salmon, masu salmon, king salmon, keta salmon, coho salmon, Danube salmon, Pacific salmon and pink salmon.

Alternatively, it may also be a feedstuff intended for farming fish which are subsequently processed to give fish meal or fish oil. These fish are preferably herring, pollack, menhaden, anchovies, caplin or cod. The fish meal or fish oil thus obtained, in turn, can be used in aquaculture for farming edible fish or crustaceans.

Aquaculture may take place in ponds, tanks, basins or else in segregated areas in the sea or in lakes, in particular in cages or net pens. Aquaculture may be used for farming the finished edible fish, but also for farming fry which are subsequently released so as to restock the wild fish stocks.

In salmon farming, the fish are preferably first grown into smolts in freshwater tanks or artificial watercourses and then grown on in cages or net pens which float in the sea and which are preferably anchored in bays or fjords.

Accordingly, a further object of the present invention is also a method for farming animals, in particular finfish or crustaceans, preferably salmon, in which a feedstuff according to the invention is employed. A further object of the present invention is additionally an animal, in particular a finfish or shellfish, which is obtainable by such a method according to the invention.

The present invention further provides methods for obtaining an oxidation-sensitive material of value from a biomass comprising a drying step in accordance with the invention.

The invention claimed is:

1. A method for drying a microbial biomass containing an oxidation-sensitive material of value, comprising a drying step in which drying gas is passed over the biomass in cycle gas mode, wherein the drying gas has an oxygen content of 5 to 13% by weight and the oxidation-sensitive material is an unsaturated fatty acid; wherein the drying gas is produced by a method consisting of heating air.

2. The method of claim 1, wherein the oxidation-sensitive material of value is an omega-3 fatty acid or an omega-6 fatty acid.

3. The method of claim 1, wherein the drying step is a fluidized bed process in which the fluidized bed has a temperature of 45 to 95° C.

4. The method of claim 1, wherein the biomass is both dried and granulated in one step.

5. The method of claim 3, wherein the fluidized bed process is operated in continuous and static mode, fermentation broth containing biomass is continuously sprayed in and the finished product is continuously discharged.

6. The method of claim 1, wherein the biomass comprises cells from the taxon Labyrinthulomycetes.

7. The method of claim 1, wherein the biomass comprises cells from the family Thraustochytriaceae.

8. The method of claim 1, wherein the biomass comprises cells from the genera *Thraustochytrium, Schizochytrium* or *Ulkenia*.

9. The method of claim 1, wherein the biomass used in the drying step is in the form of fermentation broth with a solid content of 20 to 40% by weight.

* * * * *